United States Patent [19]

Morawetz et al.

[11] Patent Number: 4,528,984
[45] Date of Patent: Jul. 16, 1985

[54] AUTOPROGRAMMABLE FUNCTIONAL ELECTRICAL STIMULATION APPARATUS AND METHOD

[75] Inventors: Peter L. Morawetz, Minneapolis; John H. Burdette, Coon Rapid, both of Minn.

[73] Assignee: EMPI, Inc., Fridley, Minn.

[21] Appl. No.: 488,124

[22] Filed: Apr. 25, 1983

[51] Int. Cl.³ ............................................. A61N 1/36
[52] U.S. Cl. ............................................................. 128/421
[58] Field of Search ................... 128/421, 422, 423 R, 128/423 W

[56] References Cited

U.S. PATENT DOCUMENTS

| | | | |
|---|---|---|---|
| 3,810,457 | 5/1974 | Bottcher et al. | 128/421 |
| 4,167,190 | 9/1979 | Sorenson et al. | 128/423 R |
| 4,390,023 | 6/1983 | Rise | 128/421 |
| 4,392,496 | 7/1983 | Stanton | 128/423 W |
| 4,408,609 | 10/1983 | Axelgaard | 128/421 |

OTHER PUBLICATIONS

Strovnik et al., "IEEE Transactions on Biomedical Engineering", vol. BME-26, No. 2, Feb., 1979, pp. 112-116.

Primary Examiner—William E. Kamm
Attorney, Agent, or Firm—Kinney & Lange

[57] ABSTRACT

A muscle stimulator provides an electrical output pulse train which provides functional electrical stimulation (FES) of muscles or muscle groups. The muscle stimulator includes a manually operated amplitude control which provides an amplitude control signal for controlling the amplitude of the output pulse train. During a PROGRAM mode, a clinician manipulates the amplitude control to establish a desired FES regimen. An analog-to-digital converter periodically samples the amplitude control signal during the PROGRAM mode, and data from the analog-to-digital converter is stored. When an EXECUTE mode is selected, the pulse width of the output pulse train is automatically controlled as a function of the stored data to reproduce the desired FES regimen which had been established during the PROGRAM mode.

43 Claims, 4 Drawing Figures

AUTOPROGRAMMABLE FUNCTIONAL ELECTRICAL STIMULATION APPARATUS AND METHOD

BACKGROUND OF THE INVENTION

1. Field of the Invention

The present invention relates to apparatus and method for electrical stimulation of muscles. In particular, the present invention relates to a programmable muscle stimulator which automatically reproduces a desired regimen of functional electrical stimulation.

2. Description of the Prior Art

Functional electrical stimulation (FES), which sometimes in a more restricted sense is called neuromuscular stimulation (NMS), is a technique of causing muscles to contract by means of an electrical current. FES is typically used therapeutically when there is a lack of neuromotor faculty, or when muscles which have been weakened or damaged by disease or trauma can benefit from a program of enforced contractions akin to voluntary exercise. In some cases, FES can be used in lieu of or complementary to exercise to strengthen an athlete's muscles. In addition, FES can be used prosthetically when voluntary motor ability is irretrievably lost, such as in certain forms of paralysis.

Muscle stimulators of various types have been developed to accomplish FES. A typical muscle stimulator consists of an electrical pulse generator and one or two pairs of electrodes (depending upon whether the pulse generator has one or two output channels). The electrodes are placed in appropriate locations on the skin, and electrical pulse trains from the pulse generator are applied transcutaneously to produce a contraction of muscles or groups of muscles. The effectiveness of the contraction is determined visually by the clinician, or by the patient himself.

The typical muscle stimulator of the prior art has controls which allow the clinician or the patient to select a stimulation regimen which is best suited for the particular purpose. In general, the controls permit selection of the pulse repetition rate (i.e. the number of pulses per second) and the pulse intensity (i.e. the amplitude, the pulse width or both). Most muscle stimulators also have a "time on" control which determines a contraction time and a "time off" control which determines a relaxation time. The clinician sets these controls to define a succession of contraction/relaxation cycles which the clinician believes is best for the desired purpose. Normally, the relaxation time is longer than the contraction time. For example, in a typical FES regimen the "time on" control may be set for a contraction time of about ten seconds, and the "time off" control may be set for a relaxation time of about twenty-five seconds.

Most muscle stimulators used for FES also include a "ramp up" control which selects a fraction of the contraction time during which the intensity of the pulses increases gradually. This prevents a sudden shock to the patient at the onset of the contraction time, and makes the contraction more naturally "physiological". In some cases, the muscle stimulator includes both a "ramp up" control and a "ramp down" control so that the slope of the pulse intensity at both the onset and the termination of the contraction time can be selected by the clinician.

When commencing the application of FES for any of the purposes described above, the clinician normally sets the stimulator to a "CONTINOUS" mode (which is defined as infinite "time on", zero "time off", and no ramp times) and also selects a pulse repetition rate. After placing the electrodes optimally on the patient's skin, the clinician proceeds to cause a contraction to occur by gradually increasing the intensity setting of the intensity control from a zero setting to a setting which produces a maximum contraction. The clinician then determines (by prior knowledge and intuition) suitable "time on", "time off", "ramp up", and "ramp down" settings. Next, the clinician submits the patient to a session at the selected regimen, and observes the effect of that regimen on the patient. Often the clinician adjusts one or more of the control settings and continues to observe the effects on the patient until a desired regimen is achieved. The patient may then be asked to continue sessions at home using the same regimen. This requires that the patient remember all of the control settings and/or make certain that none of the settings are disturbed.

There is a continuing need for improved muscle stimulators which are easier for both the clinician and the patient to use. In particular, there is a continuing need for a muscle stimulator that saves the clinician (and the patient) the laborious steps which have been performed in the past in order to arrive at a desired FES regimen.

SUMMARY OF THE INVENTION

The present invention is an improved apparatus and method for functional electrical stimulation which automatically reproduces a desired FES regimen. The apparatus includes means for selecting a PROGRAM mode during which a desired FES regimen is established, and an EXECUTE mode during which the desired FES regimen is reproduced.

During the PROGRAM mode, user-actuated control means controls the intensity of the electrical output signal of the apparatus to produce the desired FES regimen. The apparatus also includes means for periodically sampling a signal representative of the controlled intensity during the PROGRAM mode, and means for storing data based upon the sampled signal.

The FES apparatus also includes means for controlling the intensity of the output signal during the EXECUTE mode as a function of the stored data. Since the stored data represents the sampling of the controlled intensity during the PROGRAM mode, the intensity of the output signal during the EXECUTE mode automatically reproduces the desired FES regimen. The present invention, therefore, allows a desired regimen to be established simply and quickly during the PROGRAM mode, and provides automatic reproduction of that desired FES regimen later when the apparatus is in the EXECUTE mode.

DETAILED DESCRIPTION OF THE PREFERRED EMBODIMENTS

Figure 1:
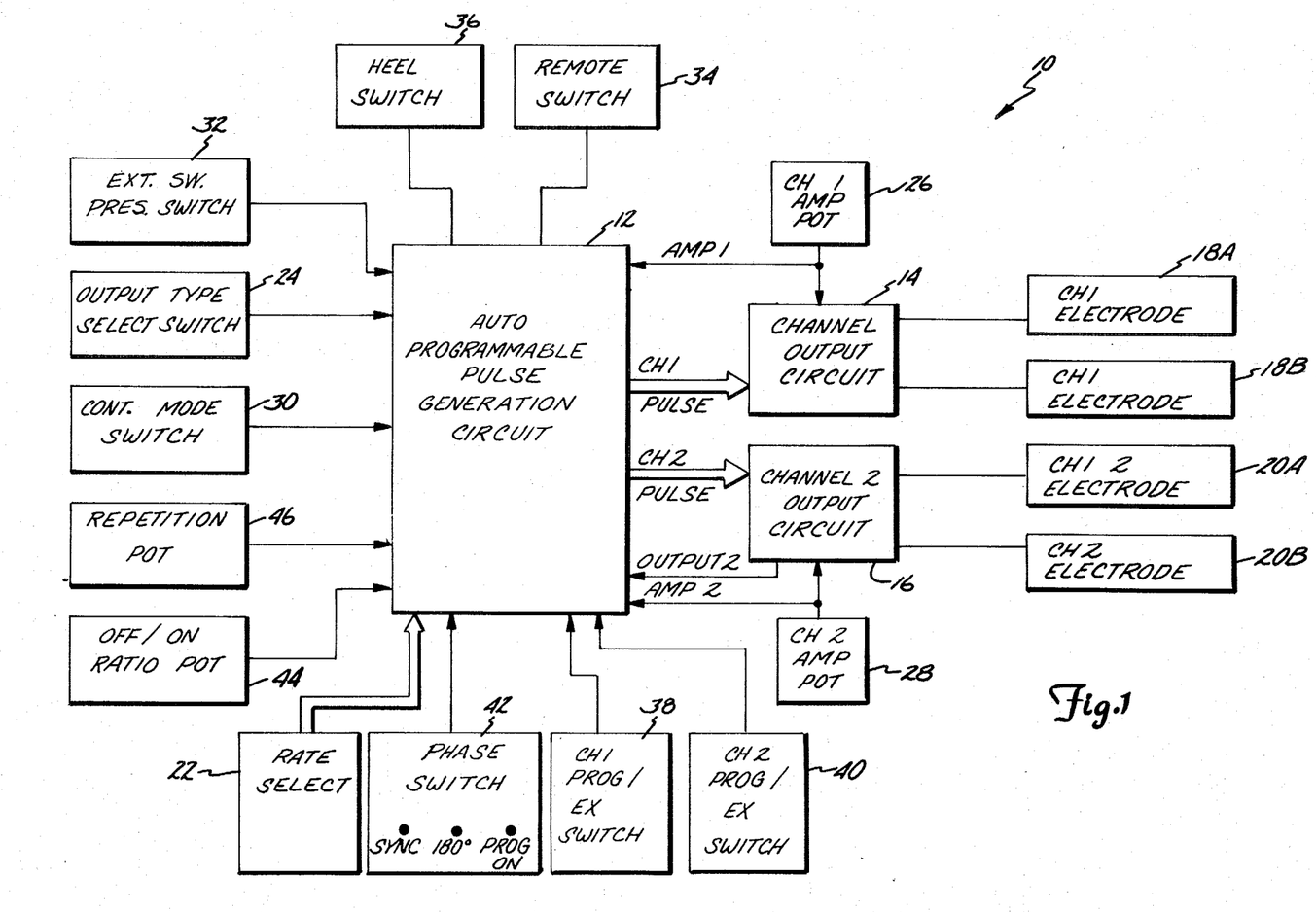
FIG. 1 is an electrical block diagram of an autoprogrammable FES muscle stimulator of the present invention.

A preferred embodiment of a dual channel muscle stimulator 10 of the present invention is shown in an electrical block diagram in FIG. 1. Muscle stimulator 10 includes autoprogrammable pulse generation circuit 12, Channel 1 output circuit 14, Channel 2 output circuit 16, Channel 1 electrodes 18A and 18B, Channel 2 electrodes 20A and 20B, Rate Select switch 22, Output Type Select switch 24, Channel 1 Amplitude potentiometer 26, Channel 2 Amplitude potentiometer 28, Continuous Mode switch 30, External Switch Present switch 32, Remote switch 34, Heel switch 36, Channel 1 Program/Execute switch 38, Channel 2 Program/Execute switch 40, Phase switch 42, OFF/ON Ratio potentiometer 44, and Repetition potentiometer 46.

Autoprogrammable pulse generation circuit 12 produces a CH1 PULSE signal which is supplied to Channel 1 output circuit 14 and a CH2 PULSE signal which is supplied to Channel 2 output circuit 16. The pulse rate of the CH1 PULSE signal and the CH2 PULSE signal is determined by the setting of Rate Select switch 22. In one preferred embodiment, the pulse rate which is selectable by Rate Select switch 22 varies from one pulse per second to ninety-nine pulses per second (i.e. 1 Hz to 99 Hz).

Channel 1 output circuit 14 produces an output pulse train to Channel 1 electrodes 18A and 18B as a function of the CH1 PULSE signal and an amplitude control signal (AMP1) from Channel 1 Amplitude potentiometer 26. Similarly, Channel 2 output circuit 16 provides an output pulse train to Channel 2 electrodes 20A and 20B as a function of the CH2 PULSE signal and an amplitude control signal (AMP2) from Channel 2 Amplitude potentiometer 28. In the preferred embodiment shown in FIG. 1, the output pulse trains provided by Channel 1 output circuit 14 and Channel 2 output circuit 16 are either monophasic or biphasic, depending upon the setting of Output Type Select switch 24.

The amplitude of the pulses of the output pulse trains produced by Channel 1 and Channel 2 output circuits 14 and 16 are controlled by Channel 1 Amplitude potentiometer 26 and Channel 1 Amplitude potentiometer 28, respectively. The Channel 1 amplitude control signal (AMP1) is provided to both Channel 1 output circuit 14, and also to pulse generation circuit 12. As discussed in further detail later, the AMP1 signal is used by pulse generation circuit 12 during the PROGRAM mode, in which a desired FES regimen is stored for later use in an EXECUTE mode.

The channel 2 amplitude control signal (AMP2) from Channel 2 Amplitude potentiometer 28 is supplied to Channel 2 output circuit 16, and also to pulse generation circuit 12. The AMP2 signal controls the amplitude of the output pulse train from Channel 2 output circuit 16, and also is used by pulse generation circuit 12 during the PROGRAM mode to produce a stored FES regimen for Channel 2 which can be replicated when muscle stimulator 10 is in the EXECUTE mode.

The preferred embodiment of muscle stimulator 10 shown in FIG. 1 is capable of operating in five different modes. These modes are, in order of priority: (1) CONTINUOUS mode; (2) REMOTE mode; (3) HEEL SWITCH mode; (4) PROGRAM mode; and (5) EXECUTE mode.

The CONTINUOUS mode is selected whenever Continuous Mode switch 30 is actuated. In the CONTINUOUS mode, output pulse trains are supplied by Channel 1 output circuit 14 and Channel 2 output circuit 16 as a function of the selected rate, output type, and amplitude. The Channel 1 and Channel 2 output pulse trains are in phase and identical in pulse width, but may differ in amplitude based upon the AMP1 and AMP2 control signals from Channel 1 Amplitude potentiometer 26 and the Channel 2 Amplitude potentiometer 28.

The CONTINUOUS mode is primarily used when the clinician is attempting to determine the proper placement of electrodes 18A, 18B, 20A and 20B. In the CONTINUOUS mode, the output pulse trains from output circuits 14 and 16 are continuous (i.e. infinite "time on" and zero "time off").

The REMOTE mode is enabled when External Switch Present switch 32 is ON and Remote switch 34 is actuated. Output pulse trains are produced by Channel 1 output circuit 14 and Channel 2 output circuit 16 as long as Remote switch 32 is actuated. When Remote switch 34 is released by the clinician, the output pulse trains cease.

The HEEL SWITCH mode also requires that External Switch Present switch 32 be ON. The HEEL SWITCH mode is used primarily for gait retraining of stroke victims. Heel switch 36 is actuated each time a patient's heel is pressed down against the floor. When Heel switch 36 is actuated, pulse generation circuit 12 supplies the CH1 PULSE and CH2 PULSE signals to output circuits 14 and 16, which in turn supply output pulse trains to electrodes 18A, 18B, 20A and 20B which are attached to the lower leg of the patient. The output pulse trains continue for a selected period of time after Heel switch 36 is actuated, e.g., about five seconds. This causes the muscles of the lower leg of the patient to be stimulated, thus causing a muscle contraction which allows the patient to lift the leg. As a result, the patient is assisted in relearning how to walk.

In the PROGRAM mode, the clinician establishes a desired FES regimen for Channel 1 or for Channel 2. The FES regimen is stored in the form of digital data by pulse generation circuit 12 for later use when muscle stimulator 10 is in the EXECUTE mode.

A desired FES regimen for Channel 1 is established during the PROGRAM mode when Channel 1 Program/Execute switch 38 is in the PROGRAM position. Pulse generation circuit 12 supplies the CH1 PULSE signal to Channel 1 output circuit 14. The CH1 PULSE signal has a repetition rate which is determined by Rate Select switch 22, and has a full pulse width (which in one preferred embodiment is about 235 microseconds).

As long as Channel 1 Amplitude potentiometer 26 is set at its minimum amplitude setting, no output pulses appear at the output of Channel 1 output circuit 14. The clinician then begins to change the setting of Channel 1 Amplitude potentiometer 26 (and thus the AMP1 signal) so that the amplitude of the output pulse train from Channel 1 output circuit 14 changes. Typically, the clinician progressively changes the setting of Channel 1 Amplitude potentiometer 26, so that the amplitude of the output pulse train from Channel 1 output circuit 14 is progressively increased until a desired maximum amplitude is achieved. This represents the "ramp up" portion of the FES regimen. Channel 1 Amplitude potentiometer 26 is then typically maintained at the desired maximum amplitude setting for a period long enough to produce the required muscle contraction. This is equivalent to the "time on" period of the FES regimen. The clinician then changes the setting of Channel 1 Amplitude potentiometer 26 to cause a progressive reduction in the amplitude of the output pulse train from Channel 1 output circuit 14 until the amplitude reaches zero. This represents the "ramp down" portion of the FES regimen.

During the PROGRAM mode, pulse generation circuit 12 periodically samples the AMP1 signal and stores a sequence of digital data based on that sampled information for use during the EXECUTE mode. The sampling rate used by pulse generation circuit 12 is sufficiently high so that the stored digital data accurately represents the variation in the AMP1 signal (and thus the variation in the amplitude of the Channel 1 output pulse train) during the PROGRAM mode. This stored digital data is used later during the EXECUTE mode in reproducing the FES regimen for Channel 1.

When Channel 1 Program/Execute switch 38 is in the PROGRAM position, only a Channel 1 FES regimen can be stored. Channel 2 Program Execute switch 40 is ignored if it is in the PROGRAM position. If Channel 2 Program/Execute switch 40 is in the EXECUTE position and Phase switch 42 is in the PROGRAM ENABLE position, a previously stored Channel 2 FES regimen will be executed while the Channel 1 FES regimen is being programmed.

A separate FES regimen for Channel 2 can be programmed in a similar manner. Channel 2 Program/Execute switch 40 is placed in the PROGRAM position, and Channel 1 Program/Execute switch 38 is placed in the EXECUTE position. The clinician then establishes the FES regimen by varying the setting of Channel 2 Amplitude potentiometer 28. The AMP2 signal from Channel 2 Amplitude potentiometer 28 is sampled by pulse generation circuit 12 when Channel 2 is in the PROGRAM mode, and a sequence of digital data based on the sequence of sampled values are stored for later use in reproducing the FES regimen for Channel 2 during the EXECUTE mode.

The EXECUTE mode has the lowest priority—in other words, pulse generation circuit 12 operates in the EXECUTE mode for a particular channel only when none of the other four modes is active for that channel.

There are several possible combinations of outputs of Channel 1 and Channel 2 output circuits 14 and 16 during the EXECUTE mode. These are (1) Channel 1 output pulse train only; (2) synchronized Channel 1 and Channel 2 output pulse trains based upon the stored Channel 1 FES regimen; (3) sequential Channel 1 and Channel 2 output pulse trains both based upon the stored Channel 1 FES regimen; (4) Channel 2 output pulse train only based upon a stored Channel 2 FES regimen; and (5) a Channel 1 output pulse train based upon a stored Channel 1 FES regimen and a Channel 2 output pulse train based upon a stored Channel 2 FES regimen.

Channel 1 is placed in the EXECUTE mode when Channel 1 Program/Execute switch 38 is in the EXECUTE position. In this case, pulse generation circuit 12 produces the CH1 PULSE signal to Channel 1 output circuit 14. The pulse width of the CH1 PULSE signal is varied as a function of the sequence of digital data representing stored Channel 1 FES regimen, so as to replicate the variation in intensity of the output pulse train which occurred during the PROGRAM mode.

If Channel 2 Amplitude potentiometer 28 is in its minimum amplitude setting, no Channel 2 output is produced regardless of the position of Channel 2 Program/Execute switch 40 and Phase switch 42. In addition, no Channel 2 output is produced if Channel 1 Program/Execute switch 40 is in the EXECUTE position, Phase switch 42 is in the PROGRAM ENABLE position, and no Channel 2 FES regimen is stored.

The patient or clinician may vary the amplitude of the Channel 1 output pulse train during the EXECUTE mode by changing the setting of Channel 1 Amplitude potentiometer 26. This allows patient or clinician to compensate for a different sensitivity which the patient may exhibit to the stored FES regimen. This changed sensitivity can be the result of slightly different electrode placement or physiological changes of the patient.

During the EXECUTE mode, OFF/ON Ratio potentiometer 44 is used to select the "time off" position of the FES regimen.

The rate of pulses produced during the EXECUTE mode is selectable by the patient by means of Rate Select switch 22. In addition, the patient can select the number of times that the stored FES regimen is to be repeated by adjusting the setting of Repetition potentiometer 46.

When Channel 1 and Channel 2 are both operated based upon the stored Channel 1 FES regimen, Channel 1 and Channel 2 Program/Execute switches 38 and 40 are placed in the "EXECUTE" position, and Phase switch 42 is placed in either the "SYNC" or the "180°" position. When Phase switch 42 is in the "SYNC" position, the CH1 PULSE and CH2 PULSE signals are identical and in phase. Both the CH1 PULSE and CH2 PULSE signals vary in pulse width as a function of the stored Channel 1 FES regimen. The amplitude of the Channel 1 output pulse train is determined by the AMP1 signal, and the amplitude of the Channel 2 output pulse train is determined by the AMP2 signal.

When Phase switch 42 is in the "180°" position, the CH2 PULSE signal from pulse generation circuit 12 is shifted in time so that it begins to "ramp up" after the CH1 PULSE signal has completed "ramp down". Both the CH1 PULSE and CH2 PULSE signals are based upon the same stored FES regimen. This shifting of the CH2 PULSE signal with respect to the CH1 PULSE signal is particularly effective when Channel 1 electrodes 18A and 18B and Channel 2 electrodes 20A and 20B are placed on the patient's body so that they sequentially activate different muscle groups which operate in different directions.

Operation of Channel 2 only in the EXECUTE mode is achieved when Channel 1 and Channel 2 Program/Execute switches 38 and 40 are in the EXECUTE position, Phase switch 42 is in the PROGRAM ENABLE position, and Channel 1 Amplitude potentiometer 26 is at the minimum amplitude setting. The pulse width of the CH2 PULSE signal is varied as a function of a stored Channel 2 FES regimen. The amplitude of the output pulse train from Channel 2 output circuit 16 is controlled by the AMP2 signal.

The production of independent Channel 1 and Channel 2 output pulse trains based upon separately stored Channel 1 and Channel 2 FES regimens is achieved by placing switches 38 and 40 in their EXECUTE positions, and Phase switch 42 in the PROGRAM ENABLE position. The CH1 PULSE signal supplied by pulse generation circuit 12 to Channel 1 output circuit 14 has pulse widths which are based upon the stored sequence of digital data of the Channel 1 FES regimen; and the CH2 PULSE signal supplied by pulse generation circuit 12 to Channel 2 output circuit 16 has pulse widths which are based upon the stored sequence of digital data for the Channel 2 FES regimen. Providing different Channel 1 and Channel 2 output pulse trains is particularly advantageous when two different muscle groups are to be activated. For example, in one such application the Channel 1 output pulse train stimulates muscles which cause the patient's lower arm to be lifted, while the Channel 2 output pulse train stimulates muscles which cause the patient's hand to be moved in a particular manner.

Figure 2A:
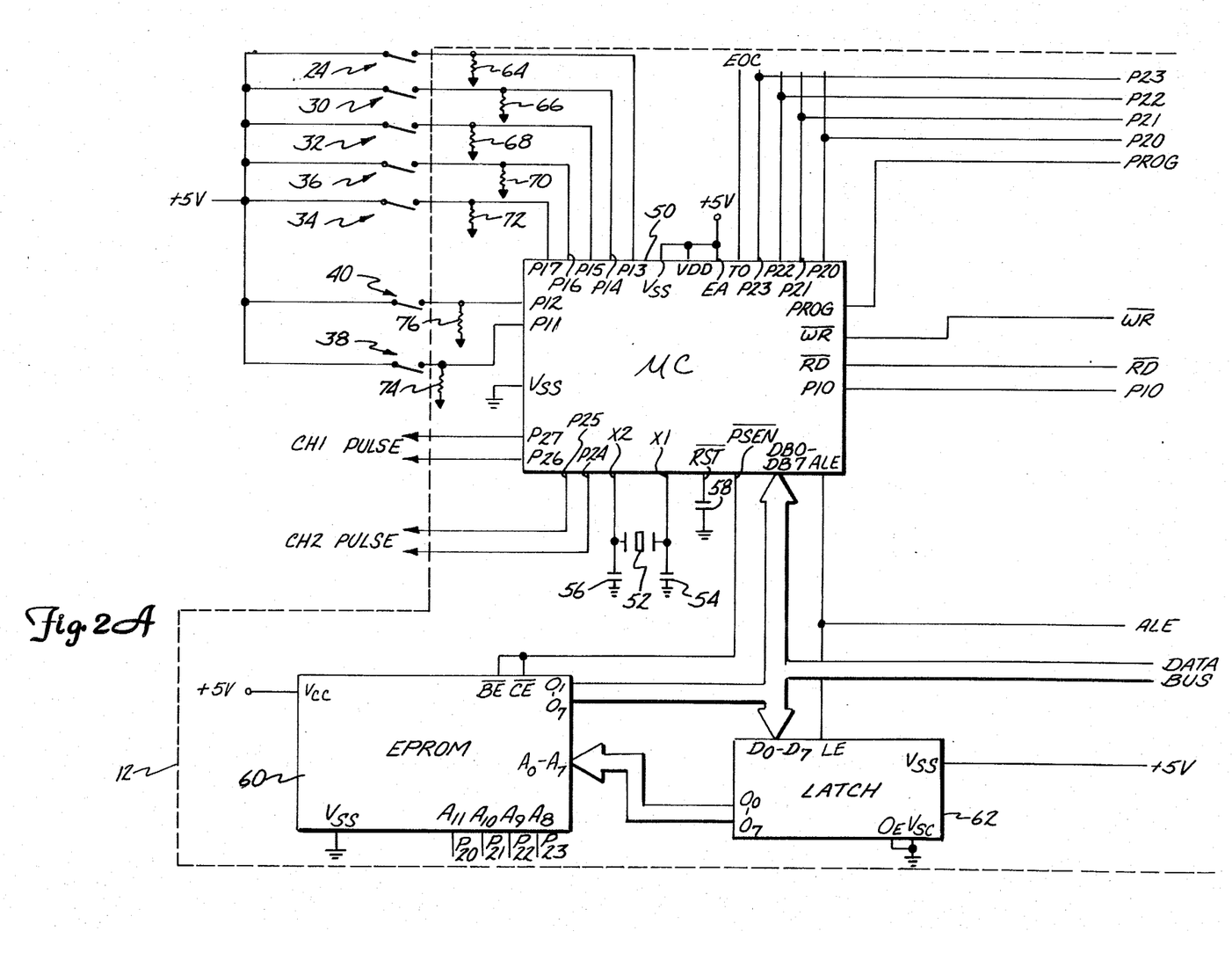
FIGS. 2A and 2B are a more detailed electrical schematic diagram of a portion of the muscle stimulator of FIG. 1.
Figure 2B:
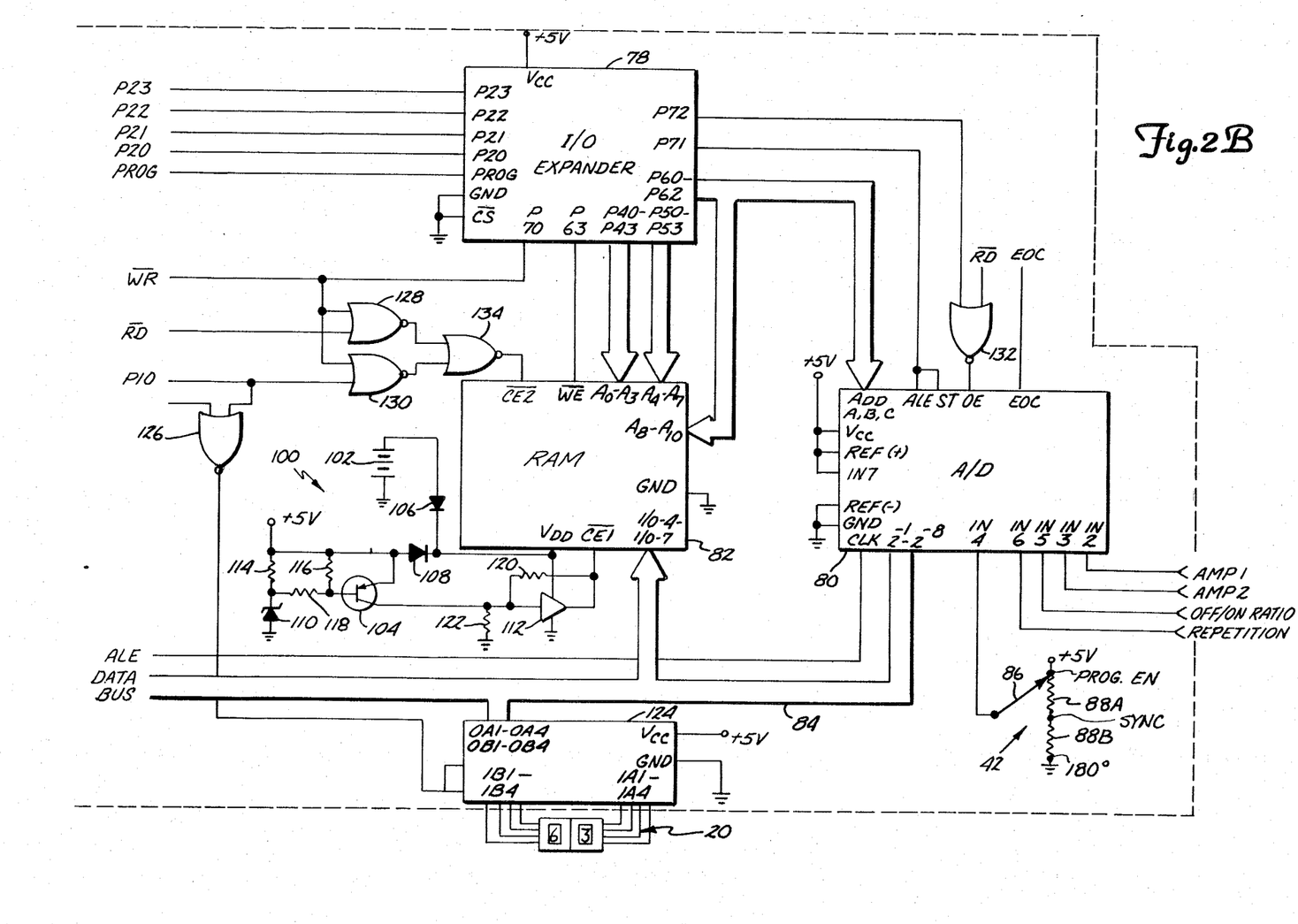

FIGS. 2A and 2B are an electrical schematic diagram of a portion of muscle stimulator 10 of FIG. 1. The portion shown in FIGS. 2A and 2B includes autoprogrammable pulse generation circuit 12, Rate Select switch 22, Output Type Select switch 24, Continuous Mode switch 30, External Switch Present switch 32, Remote switch 34, Heel switch 36, Channel 1 Program/Execute switch 38, Channel 2 Program/Execute switch 40, and Phase switch 42.

The processing function of autoprogrammable pulse generation circuit 12 is performed by microcomputer 50 shown in FIG. 2A. Microcomputer 50, in the embodiment shown in FIG. 2A, is preferably an eight-bit 80C39 CMOS microcomputer which contains 128 bytes of random access memory for scratch pad memory, 27 input/output lines and an eight-bit time/counter. Microcomputer 50 provides the basic logic, arithmetic and control capability for pulse generation circuit 12. Crystal oscillator 52 and capacitors 54, 56 and 58 are connected to microcomputer 50 to provide basic timing and reset functions.

Erasable programmable read only memory (EPROM) 60 stores constants and instructions for use by microcomputer 50 in controlling the operation of pulse generation circuit 12. EPROM 60 is addressed by microcomputer 50 through latch 62.

Microcomputer 50 monitors the status of Output Type Select switch 24 through its P13 port. One terminal of switch 24 is connected to +5 volts, and the other terminal is connected to port P13. Input resistor 64 is connected between port P13 and ground.

Microcomputer 50 monitors the status of Continuous Mode switch 30 through port P14. One terminal of switch 30 is connected to +5 volts, and the other terminal is connected to port P14. Input resistor 66 is connected between port P14 and ground.

External Switch Present switch 32 has one terminal connected to +5 volts and the other terminal connected to port P15 of microcomputer 50. Input resistor 68 is connected between port P15 and ground.

Heel switch 36 has one terminal connected to +5 volts and the other connected to port P16 of microcomputer 50. Input resistor 70 is connected between port P16 and ground.

Remote switch 34 is connected between +5 volts and port P17 of microcomputer 50. Input resistor 72 is connected between port P17 and ground.

Channel 1 Program/Execute switch 38 is connected between +5 volts and port P11, while Channel 2 Program/Execute switch 40 is connected between +5 volts and port P12. Input resistor 74 is connected between port P11 and ground, while input resistor 76 is connected between port P12 and ground.

Microcomputer 50 monitors the status of the switches connected to ports P11 through P17, and determines which operating mode is active based upon the status of the switches. As discussed previously, the CONTINUOUS mode (which is activated when switch 30 is closed) has highest priority, while the EXECUTE mode (selected by switches 38 and 40) has the lowest priority.

Microcomputer 50 provides the CH1 PULSE signal to Channel 1 output circuit 14 through its P26 and P27 ports. Only Port P27 is active when a monophasic output has been selected by switch 24, and both ports P26 and P27 are active when a biphasic output has been selected.

Similarly, the CH2 PULSE signal is supplied by microcomputer 50 to Channel 2 output circuit through ports P25 and P24. Only Port P25 is active if a monophasic output has been selected; while both ports P25 and P24 are active if a biphasic output has been selected.

Because the total number of input/output lines required in pulse generation circuit 12 exceeds the number of input/output lines available from microcomputer 50, pulse generation circuit 12 includes input/output (I/O) expander 78 (FIG. 2B) which is connected to ports P20 through P23 and the PROG line of microcomputer 50. I/O expander 78 allows microcomputer 50 to address analog-to-digital converter 80 and random access memory 82. Data bus 84 carries data from A/D converter 80 to microcomputer 50, and also allows microcomputer 50 to read data from or write data to RAM 82.

In a preferred embodiment of the present invention, A/D converter 80 is an ADC0809CCN analog-to-digital converter chip which includes an eight-bit A/D converter together with an eight-channel multiplexer. The inputs to A/D converter 80 include the AMP1 signal, the AMP2 signal, a signal from OFF/ON Ratio potentiometer 44, a signal from Repetition potentiometer 46, and a signal from Phase switch 42. A/D converter 80 samples the input which is selected by microcomputer 50, and converts the analog input signal received to digital data. A/D converter 80 supplies an end-of-conversion (EOC) signal to the TO input of microcomputer 50, to signal that the conversion has been completed. The data is then read by microcomputer 50 from A/D converter 80 through data bus 84.

As shown in FIG. 2B, Phase switch 42 consists of a three-position switch 86 and a pair of resistors 88 and 90. The "Program Enable" terminal of switch 86 is connected to +5 volts, and the "180°" terminal is connected to ground. Resistor 88 is connected between the Program Enable terminal and the "Sync" terminal, and resistor 90 is connected between the Sync terminal and the 180° terminal. Depending upon the position of Phase switch 42, A/D converter 80 receives a signal of 5 volts, ground, or an intermediate voltage (typically 2.5 volts).

RAM 82 preferalby contains 2K bytes of static RAM storage. The sampled data produced by A/D converter 80 during the PROGRAM mode is stored in RAM 82 for later use during the EXECUTE mode. The contents of RAM 82 are maintained even when muscle stimulator 10 is turned off by means of a backup power supply circuit 100, which includes battery 102, transistor 104, diodes 106 and 108, Zener diode 110, buffer 112, and resistors 114, 116, 118, 120 and 122.

Rate Select switch 22 is, in the embodiment shown in FIG. 2B, a two-digit thumbwheel switch. Rate Select switch 22 is interfaced with data bus 84 through tristate buffer 124. An eight-bit, two-digit binary coded decimal (BCD) word representing the selected rate is supplied by tristate buffer 124 to microcomputer 50 on data bus 84.

Pulse generation circuit 12 also includes NOR gates 126, 128, 130 and 132 and OR gate 134. These logic gates are provided to avoid output clashes among A/D converter 80, RAM 82 and tristate buffer 124, all of which communicate with microcomputer 50 on data bus 84.

Figure 3:
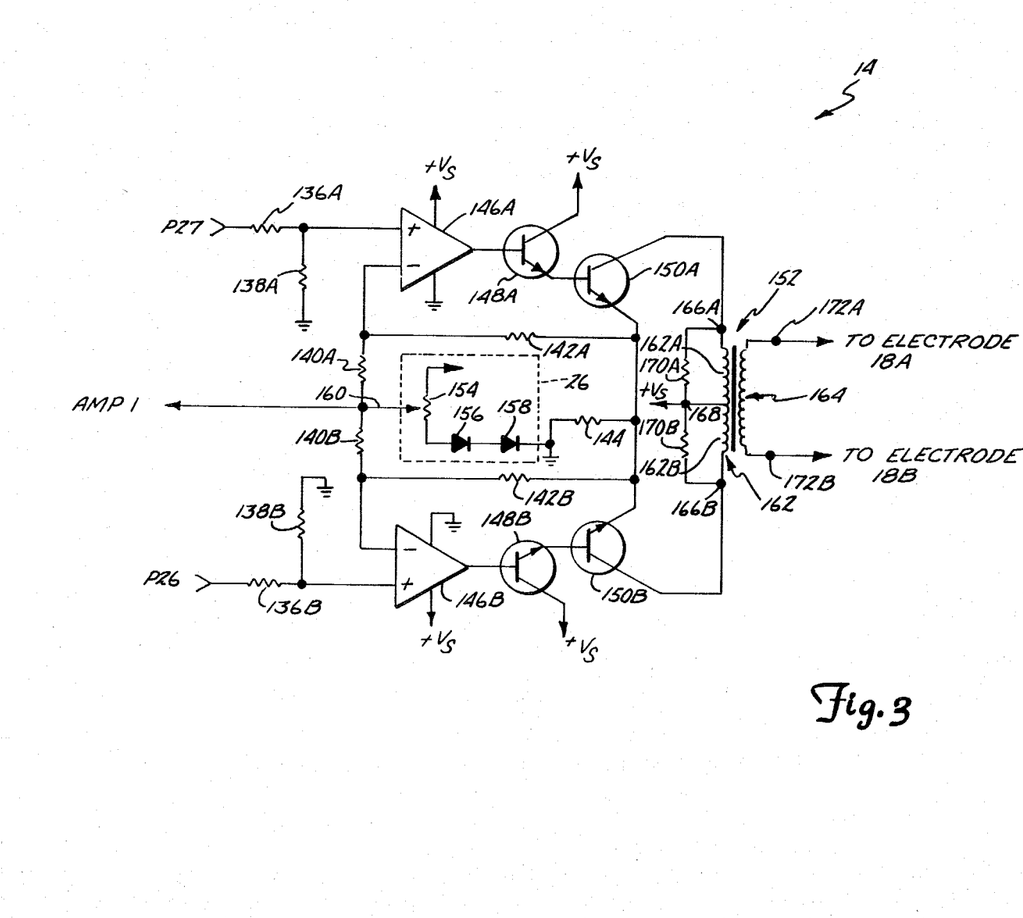
FIG. 3 is an electrical schematic diagram of the Channel 1 output circuit of the muscle stimulator of FIG. 1.

FIG. 3 is an electrical schematic diagram of Channel 1 output circuit 14 and Channel 1 Amplitude potentiometer 26. In a preferred embodiment of the present invention Channel 2 output circuit 16 is of identical construction to Channel 1 output circuit 14, and therefore only Channel 1 output circuit 14 will be discussed in detail.

Output circuit 14 of FIG. 3 produces either a monophasic or biphasic output pulse train, depending upon whether the CH1 PULSE signal is received from port P27 only, or from both ports P27 and P26. The portion of output circuit 14 which converts the signal from port P27 to an output pulse includes resistors 136A, 138A, 140A, 142A, and 144, operational amplifier (op amp) 146A, transistors 148A and 150A, and transformer 152. The portion of output circuit 14 which converts the signal from port P26 to an output pulse includes resistors 136B, 138B, 140B, 142B and 144, op amp 146B, transistors 148B and 150B, and transformer 152.

In the embodiment shown in FIG. 3, the CH1 PULSE signal from the port P27 is received by a voltage divider formed by resistors 136A and 138A. Op amp 146A has its noninverting (+) input connected to the junction of resistors 136A and 138A to receive the pulse train from port P27.

The inverting (−) input of op amp 146A receives a reference voltage which is based upon the setting of Channel 1 Amplitude potentiometer 26. In the embodiment shown in FIG. 3, potentiometer 26 includes a resistive element 154 connected in series with diodes 156 and 158 between +5 volts and ground. Wiper arm 160 of potentiometer 26 is connected through a voltage divider formed by resistors 140A, 142A and 144 to ground. The inverting (−) input of op amp 146A is connected to the junction of resistors 140A and 142A. The voltage (control signal AMP1) at the wiper arm 160 of potentiometer 26 determines the voltage at the inverting input and, therefore, determines the amplitude of the output of op amp 146A. The higher the voltage at the inverting input, the smaller the amplitude of the output of op amp 146A.

The output of operational amplifier 146A is supplied to the base of NPN transistor 148A. The collector of transistor 148A is connected to the $+V_S$ power supply voltage, and the emitter of transistor 148A is connected to the base of NPN transistor 150A. The emitter of transistor 150A is connected through resistor 144 to ground.

In the embodiment shown in FIG. 3, transformer 152 has a center tap primary 162 and a secondary 164. Primary winding 162A of primary 162 is connected between terminal 166A and center tap terminal 168, and primary winding 162B of primary 162 is connected between terminal 166B and center tap terminal 168. Resistors 170A and 170B are connected in parallel with primary windings 162A and 162B, respectively. The positive supply voltage $+V_S$ is connected to center tap terminal 168.

The collector of transistor 150A is connected to terminal 166A of transformer 152 so that when transistor 150A turns on, a current path is established from center tap terminal 168 (which is connected to supply voltage $+V_S$) through primary winding 162A, through the collector-emitter current path of transistor 150A, and through resistor 152 to ground. This induces an output pulse between output terminals 172A and 172B of secondary 164. As shown in FIG. 3, output terminal 172A is connected to electrode 18A, and output terminal 172B is connected to electrode 18B. The output pulse which is produced when transistor 150A is turned on is a "positive going" pulse (i.e. output terminal 172A goes positive with respect to output terminal 172B). The amplitude of the output pulse is a function of the AMP1, and the pulse width is determined by the pulse width of the CH1 PULSE signal from port P27.

When muscle stimulator 10 is operating with a monophasic output, only positive going pulses are produced between terminals 172A and 172B based upon pulses received from the P27 port of microcomputer 50.

When a biphasic output is selected by Output Select switch 24, pulses are received from both the P27 port and the P26 port of microcomputer 50. Each pulse at the P26 port has a rising edge which occurs at the same time as the falling edge of the pulse at the P26 port. The pulses received from the P26 port produce a "negative going" pulse between output terminals 172A and 172B of secondary 162.

The pulse received from the P26 port of microcomputer 50 is supplied to a voltage divider formed by resistors 136B and 138B. The noninverting (+) input of op amp 146B receives the divided voltage from the junction of resistors 136B and 138B. The inverting (−) input of op amp 146B receives a reference voltage based upon the setting of potentiometer 26. The AMP1 voltage from wiper arm 160 is divided by resistors 140B, 142B and 144 to provide the reference voltage to the inverting (−) input of op amp 146B.

The output of op amp 146B is supplied to the base of transistor 148B. The collector of transistor 148B is connected to the $+V_S$ supply voltage, and the emitter of transistor 148B is connected to the base of transistor 150B. The emitter of transistor 150B is connected through resistor 144 to ground. The collector of transistor 150B is connected to terminal 166B of transformer 152.

The amplitude of the output pulse at the output of op amp 146B is a function of the reference voltage supplied to its inverting (−) input. This reference voltage is based upon the setting of potentiometer 26. When potentiometer 26 is at its minimum output setting (at which the AMP1 voltage at wiper arm 160 is +5 volts), the signal level of the pulse from port P26 which appears at the noninverting (+) input of op amp 146B is not sufficient to produce a pulse at the output of op amp 146B. As the AMP1 voltage at wiper arm 160 is reduced, the reference voltage at the inverting (−) input is reduced and the amplitude of the pulse at the output of op amp 146B increases, thus increasing the amplitude of the current flow through transistors 148B and 150B.

When transistor 150B is turned on, current flows from center tap terminal 168 through primary winding 162B, through the collector-emitter current path of transistor 150B, and through resistor 144 to ground. This induces a negative going output pulse between terminals 172A and 172B. The amplitude of the negative going output pulse is a function of the AMP1 voltage, and the pulse width is determined by the pulse width of the CH1 PULSE signal from port 26.

When a biphasic output is selected, therefore, the output pulse which appears between terminals 172A and 172B is first positive going as a result of the pulse from port P27 and then negative going as a result of the pulse from port P26.

With either the biphasic or monophasic output, the rate at which output pulses are produced and the pulse widths of those output pulses are determined by the CH1 PULSE signals received from the P27 and P26 ports of microcomputer 50. The amplitude of the output pulse train is determined by the clinician or the patient based upon the setting of Channel 1 Amplitude potentiometer 26. With potentiometer 26, it is possible to turn the output pulse train off entirely (i.e. an output amplitude of zero) up to a maximum amplutude which, in one preferred embodiment, is about 70 milliamps for both the positive going pulse and the negative going pulse.

The operation of the preferred embodiment shown in FIGS. 2A, 2B and 3 is generally as follows. When Continuous Mode switch 30 is closed, microcomputer 50 operates pulse generation circuit 12 in the CONTINUOUS mode. The operation in this mode is based upon instructions contained in EPROM 60. If Output Type Select switch 24 has selected a monophasic output, microcomputer 50 supplies pulses to output circuits 14 and 16 at the P27 and P25 ports, respectively. If, on the other hand, Output Type Select switch 24 has selected a biphasic output pulse, the CH1 PULSE signal is supplied at boht ports P26 and P27, and the CH2 PULSE signal is supplied at both ports P24 and P25. The pulses produced by microcomputer 50 in the CONTINUOUS mode are full pulse width and are produced at a rate which is determined by the setting of Rate Select switch 22.

As discussed previously, microcomputer 50 has an internal timer/counter. After each pulse is generated, microcomputer 50 reads tristate buffer 124 to determine the selected pulse rate. Based upon that selected pulse rate, microcomputer 50 sets the timer/counter to determine the interval until the next pulse is to be produced.

The REMOTE mode has the second highest priority. This mode is actuated when External Switch Present switch 32 and Remote switch 34 are closed. The pulse rate is determined by the setting of Rate Select switch 22, and the output type is determined by the setting of Output Type Select switch 24. The CH1 PULSE signal and CH2 PULSE signal provides to output circuits 14 and 16 and have the full pulse width. The amplitudes of the output pulses supplied to electrodes 18A and 18B and 20A and 20B are determined by the settings of Channel 1 and Channel 2 Amplitude potentiometers 26 and 28, respectively.

The HEEL SWITCH mode has the third highest priority. This mode requires that External Switch Present switch 32 be closed. Each time Heel switch 36 is closed, microcomputer 50 generates the CH1 PULSE and CH2 PULSE signals for a predetermined period (e.g., five seconds). The pulse rate is determined by Rate Select switch 22 and the output type is determined by Output Type Select switch 24. The amplitudes of the output pulse trains are determined by potentiometers 26 and 28. Once again, full pulse widths are produced by microcomputer 50 in the HEEL SWITCH mode.

The PROGRAM mode is the fourth highest priority, and is initiated when Channel 1 Program/Execute switch 38 is in the "PROGRAM" position, or when Channel 2 Program/Execute switch 40 is in the "PROGRAM" position (which in the embodiment shown in FIG. 2 is the closed position).

Depending upon which switch 38 or 40 is in the PROGRAM position, microcomputer 50 will produce a CH1 PULSE or a CH2 PULSE signal having a full pulse width and a rate which is determined by the setting of Rate Select switch 22. As the clinician varies the settings of potentiometer 26 (or 28), A/D converter 80 samples the AMP1 (or AMP2) signal. The sampling rate of A/D converter 80 is sufficiently high so that it is faster than any reasonably expected change in the AMP1 (or AMP2) signal. The digital sample values produced by A/D converter 80 during the PROGRAM mode are inverted by microcomputer 50 and the resulting digital data are stored in RAM 82. The inversion of the digital sample values from A/D converter 80 is performed because the AMP1 (or AMP2) signal has an inverse relationship to the amplitude of the output pulse train. By inverting the digital sample values, microcomputer 50 produces and stores a sequence of digital data values which have a direct rather than an inverse relationship to the desired output pulse intensity. In one preferred embodiment, each digital data value in the sequence corresponds to a decimal value of 0 to 255. Microcomputer 50 also determines and stores the maximum digital data value produced during the PROGRAM mode (which corresponds to the maximum amplitude commanded by the clinician). This maximum digital data value corresponds to the full pulse width (e.g. 235 microseconds) during the EXECUTE mode. All digital data values which are less than the stored maximum value produce a proportionally shorter pulse width.

The EXECUTE mode has the fifth and lowest priority. This mode is selected when Channel 1 Program/Execute switch 38 is in the EXECUTE position, or when Channel 2 Program/Execute switch 40 is in the EXECUTE position and Phase switch 42 is in the PROGRAM ENABLE position.

When Channel 1 Program/Execute switch 38 is in the EXECUTE position, microcomputer 50 produces the CH1 PULSE signal. The pulse rate of the CH1 PULSE signal is determined by the setting of Rate Select switch 22, which is interrogated by microcomputer 50 through tristate buffer 124. Pulses appear only at the P27 port or at both the P27 and P26 ports, depending upon the state of Output Type Select switch 24.

The pulse width of the CH1 PULSE signal produced by microcomputer 50 vaires as a function of the stored data in RAM 82. Typically, the pulse widths increase during the "ramp up" portion of the FES regimen, remain constant during the "time on" portion of the regimen, and decrease during the "ramp down" portion of the regimen. The pulses remain off for the "time off" portion of the regimen, after the end of the "ramp down" portion.

Microcomputer 50 periodically retrieves a digital data value from RAM 82 in the same sequence that the values were stored. The pulse width of each pulse is based upon the current digital data value and the maximum digital data value. For example, if the current value is 45 and the maximum value is 225, the pulse width is 45/225×235 microseconds=47 microseconds. The pulse width is generated by microcomputer 50 based upon the calculated value using a timing routine in which the necessary number of instructions are performed to correspond to the pulse width duration. The pulse width is used until the next digital data value in the sequence is retrieved from RAM 82 by microcomputer 50.

The "time off" portion of the FES regimen is determined by means of OFF/ON Ratio potentiometer 44. During each pass through its normal routine during the EXECUTE mode, microcomputer 50 causes A/D converter 80 to sample the voltage from OFF/ON Ratio potentiometer 44. If the value is nonzero, it is used by microcomputer 50 to determine the length of the "time off" period.

Microcomputer 50 repeats the stored FES regimen Channel 1 the number of times requested by Repetition potentiometer 46. Microcomputer 50 periodically reads the value of Repetition potentiometer 46 by means of A/D converter 80.

When Channel 1 is in the EXECUTE mode, an output pulse train can be provided for Channel 2 based upon the stored Channel 1 FES regimen by placing Channel 2 Operation Select switch 42 in the "SYNC" or "180°" position. Microcomputer 50 interrogates the status of switch 42 through A/D converter 80. When switch 42 is in the SYNC position, and Channel 1 Program/Execute switch 38 is in the EXECUTE position, the CH1 PULSE and CH2 PULSE signals produced by microcomputer 50 are identical and in phase.

When Channel 2 Operation Select Switch 42 is in the "180°" position, a sequential operation of Channel 1 and Channel 2 is produced. Microcomputer 50 first generates the CH1 PULSE signal based upon the stored FES regimen for Channel 1 until "ramp down" is complete, and then produces the CH2 PULSE signal based upon the same stored FES regimen for Channel 1.

When switch 42 is in the PROGRAM ENABLE position and both switches 38 and 40 are in the EXECUTE position, microcomputer 50 generates different CH1 PULSE and CH2 PULSE signals. The CH1 PULSE signal is based upon the stored sequence of digital data values in RAM 82 for a desired Channel 1 FES regimen, and the CH2 PULSE signal is based upon the stored sequence of digital data values for a desired Channel 2 FES regimen. The pulse widths of the CH1 PULSE and CH2 PULSE signals are varied periodically by microcomputer 50 as a function of the current Channel 1 and Channel 2 digital data values which have been retrieved from RAM 82 and maximum values in RAM 82 in order to replicate the variations in the AMP1 and AMP2 signals received during the PROGRAM mode.

During the EXECUTE mode, the patient can vary the amplitude of the output pulse train supplied to electrodes 18A and 18B by varying the setting of Channel 1 Amplitude potentiometer 26. Similarly, the amplitude of the output pulse train supplied by to Channel 2 electrodes 20A and 20B can be varied during the EXECUTE mode by means of Channel 2 Amplitude potentiometer 28. This is an advantageous feature, since the patient often wishes to repeat the FES treatment in the EXECUTE mode days or even weeks after the clinician initially establishes the FES regimen in the PROGRAM mode. The ability to vary the amplitude of the output pulse trains during the EXECUTE mode allows the patient to compensate for slightly different electrode placement or for different sensitivity to the output pulses at the time when the EXECUTE mode is performed.

In conclusion, the muscle stimulator of the present invention is an extremely effective yet simple-to-use device for both the patient and the clinician. With the present invention, a desired FES regimen in one or two channels is easily and quickly established without the laborious trial and error setting and resetting of multiple time controls. Even a relatively untrained clinician can establish the desired FES regimen. Once established, the stored FES can be recalled and replicated essentially indefinitely. When the clinician wishes to change the regimen, reprogramming is effected just as quickly and effortlessly. Finally, the patient does not need to recall numerous control settings in order to reproduce the FES regimen. Instead, the patient merely needs to select the EXECUTE mode for the desired channels, and pulse generation circuit 12 automatically reproduces the stored FES regimen.

Although the present invention has been described with reference to preferred embodiments, workers skilled in the art will recognize that changes may be made in form and detail without departing from the spirit and scope of the invention.

What is claimed is:

1. A functional electrical stimulation (FES) apparatus for providing an electrical output signal which is applied to a patient's body to cause contraction of muscles, the FES apparatus comprising:
    means for producing the electrical output signal;
    means for selecting a program mode of operation during which a desired FES regimen is established;
    means for varying intensity of the output signal with time during the program mode to produce the desired FES regimen;
    means for periodically sampling a signal representative of the intensity during the program mode;
    means for storing digital data based upon the periodic sampling;
    means for selecting an execute mode of operation during which the desired FES regimen is reproduced; and
    means for varying the intensity of the output signal with time during the execute mode as a function of the stored digital data to reproduce the desired FES regimen.

2. The apparatus of claim 1 wherein the output signal is an output pulse train.

3. The apparatus of claim 2 wherein the means for varying the intensity of the output signal with time during the program mode varies amplitude of output pulses of the output pulse train.

4. The apparatus of claim 3 wherein the means for varying the intensity of the output signal with time during the execute mode varies pulse width of the output pulses of the output pulse train.

5. The apparatus of claim 4 wherein the stored digital data is a sequence of digital data values representative of the amplitude of the output pulses during a sequence of time periods of the program mode of operation.

6. The apparatus of claim 5 wherein during each of a sequence of time periods of the execute mode the means for varying the intensity of the output signal with time during the execute mode causes the output pulses to have a pulse width which is a function of a selected digital data value from the sequence of digital data.

7. The apparatus of claim 6 and further comprising:
    means for storing a maximum value representative of a maximum amplitude attained during the program mode; and
    wherein during each time period of the execute mode the pulse width of the output pulses is a function of the selected digital data value and the maximum digital value.

8. The apparatus of claim 1 wherein the means for varying the intensity of the output signal during the execute mode generates pulse signals having pulse widths which vary with time as a function of the stored digital data, and wherein the means for producing the electrical output signal produces an output pulse train having pulse widths which are a function of the pulse widths of the pulse signals.

9. A functional electrical stimulation (FES) apparatus for providing an electrical output pulse train which is applied to the patient's body to cause a desired FES regimen of contraction and relaxation of muscles of the patient, the FES apparatus comprising:
  means for producing the output pulse train;
  means for selecting a program mode of operation during which the desired FES regimen is established;
  means for providing an intensity control signal during the program mode;
  means for controlling the intensity of the output pulse train during the program mode as a function of the intensity control signal;
  means for storing, during the program mode, a sequence of digital data as a function of the intensity control signal, the stored sequence being representative of the desired FES regimen;
  means for selecting an execute mode of operation during which the desired FES regimen is reproduced; and
  means for controlling the intensity of the output pulse train during the execute mode as a function of the stored sequence of digital data.

10. The apparatus of claim 9 wherein the intensity control signal is an amplitude control signal and the means for controlling the intensity of the output pulse train during the program mode controls pulse amplitude of the output pulse train as a function of the amplitude control signal.

11. The apparatus of claim 10 wherein the means for controlling the intensity of the output pulse train during the execute mode controls pulse width of the output pulse train during the execute mode as a function of the stored sequence of digital data.

12. The apparatus of claim 11 wherein during each of a sequence of time periods of the execute mode, the means for controlling the intensity of the output pulse train during the execute mode selects a digital data value from the stored sequence and wherein the pulse width of the output pulse generated during the time period is a function of the selected digital data value.

13. The apparatus of claim 12 and further comprising:
  means for storing a maximum value representative of a maximum pulse amplitude of the output pulse train attained during the program mode; and
  wherein during each time period of the execute mode the pulse width of the output pulses is a function of the selected digital data value and the maximum value.

14. The apparatus of claim 9 and further comprising:
  means for selecting a pulse rate at which output pulses of the output pulse train are produced.

15. The apparatus of claim 9 and further comprising:
  means for selecting a number of times that the desired FES regimen is repeated during the execute mode of operation.

16. The apparatus of claim 9 and further comprising:
  means for selecting a time off period of the desired FES regimen during which no output pulses are produced during the execute mode.

17. A functional electrical stimulation (FES) apparatus for causing a desired FES regimen of contraction and relaxation of muscles of a patient, the apparatus comprising:
  first channel amplitude control means for providing a first amplitude control signal;
  first program/execute select means for selecting between a first program mode of operation and a first execute mode of operation;
  pulse rate select means for selecting a pulse repetition rate;
  means for periodically sampling the first amplitude control signal during the first program mode to produce a sequence of first sample values;
  means for storing a sequence of first digital data based upon the first sample values during the program mode;
  first pulse generation means for generating a first pulse signal at the selected pulse repetition rate, the first pulse signal having a constant pulse width during the program mode of operation and having a pulse width which varies as a function of the stored sequence of first digital data during the first execute mode of operation; and
  first channel output means for providing a first output pulse train for application to the patient's body, the first output pulse train having an amplitude which is a function of the first amplitude control signal and having a pulse width which is a function of the pulse width of the first pulse signal.

18. The apparatus of claim 17 and further comprising:
  second channel amplitude control means for providing a second amplitude control signal;
  second program/execute select means for selecting between a second program mode of operation and a second execute mode of operation;
  means for periodically sampling the second amplitude control signal during the second program mode to produce a sequence of second sample values;
  means for storing a sequence of second digital data based upon the second sample values during the program mode;
  second pulse generation means for generating a second pulse signal at the selected pulse repetition rate, the second pulse signal having a constant pulse width during the second program mode of operation and having a pulse width which varies as a function of the stored sequence of second digital data during the second execute mode of operation; and
  second channel output means for providing a second output pulse train for application to the patient's body, the second output pulse train having an amplitude which is a function of the second amplitude control signal and having a pulse width which is a function of the pulse width of the second pulse signal.

19. The apparatus of claim 18 and further comprising:
  means for providing a select signal to the second pulse generation means which causes the second pulse signal to be produced during the first execute mode of operation with a pulse width which is a function of the stored sequence of first digital data.

20. The apparatus of claim 19 wherein the select signal has a first state which causes the second pulse signal to be in phase with the first pulse signal and a second state which causes the second pulse signal to be delayed in time with respect to the first pulse signal.

21. The apparatus of claim 17 and further comprising:
means for storing a maximum value representative of a maximum pulse amplitude of the first output pulse train attained during the first program mode; and
wherein during the first execute mode the first pulse generation means causes the first pulse signal to have a pulse width which is a function of the maximum value and the sequence of first digital data.

22. The apparatus of claim 17 and further comprising:
means for selecting a number of times that the desired FES regimen based upon the stored sequence of first digital data is repeated during the first execute mode of operation.

23. A method for generating functional electrical stimulation (FES) signals which are applied to a patient's body to produce a desired FES regimen of contraction and relaxation of the patient's muscles, including:
producing during a program mode a first signal of varying intensity representative of a desired FES regimen;
applying the first signal to the patient's body to produce the desired FES regimen;
periodically sampling a signal representative of the first signal;
storing digital data based upon the periodic sampling;
producing during an execute mode a second signal of varying intensity based upon the stored digital data; and
applying the second signal to the patient's body to reproduce the desired FES regimen.

24. The method of claim 23 and producing the first and second signals in the form of first and second pulse trains, respectively.

25. The method of claim 24 and varying amplitude of the pulses of the first pulse train to vary intensity of the first signal.

26. The method of claim 25 and varying pulse width of the pulses of the second pulse train to vary intensity of the second signal.

27. The method of claim 26 and storing the digital data as a sequence of digital data values representative of the amplitude of the pulses of the first pulse train.

28. The method of claim 27 and varying the pulse width of the pulses of the second pulse train as a function of the digital data values.

29. The method of claim 28 and storing maximum value data representative of a maximum amplitude of the pulses of the first pulse train.

30. The method of claim 29 and varying the pulse width of the pulses of the second pulse train as a function of the digital data values and the maximum data value.

31. A method for generating functional electrical stimulation (FES) signals which are applied to a patient's body to produce a desired FES regimen of contraction and relaxation of the patient's muscles, including:
providing a first output pulse train;
providing a first intensity control signal;
controlling intensity of the first output pulse train as a function of the first intensity control signal during a program mode;
storing a sequence of digital data as a function of the intensity control signal;
providing a second output pulse train; and
controlling intensity of the second output pulse train as a function of the stored sequence of digital data during an execute mode.

32. The method of claim 31 wherein controlling intensity of the first output pulse train comprises controlling pulse amplitude of the first output pulse train as a function of the first intensity control signal during the program mode.

33. The method of claim 32 wherein controlling intensity of the second output pulse train comprises controlling pulse width of the second output pulse train as a function of the stored sequence of digital data during the execute mode.

34. The method of claim 33 and storing maximum value data representative of a maximum pulse amplitude of the first output pulse train during the program mode.

35. The method of claim 34 wherein controlling pulse width of the second output pulse train during the execute mode is as a function of the stored sequence of digital data and the stored maximum value data.

36. The method of claim 31 and selecting a pulse rate at which output pulses of the first and second output pulse train are produced.

37. The method of claim 31 and selecting a number of times that the desired FES regimen is repeated during the execute mode.

38. The method of claim 37 and selecting a time off period of the desired FES regimen during which no output pulses are produced during the execute mode.

39. A method for producing functional electrical stimulation (FES) signals which are applied to a patient's body to cause a desired FES regimen of contraction and relaxation of the patient's muscles, including:
providing a first channel output pulse train;
providing a first amplitude control signal;
controlling pulse amplitude of the first channel pulse train as a function of the first amplitude control signal during a program mode to produce the desired FES regimen;
storing digital data representative of the first amplitude control signal; and
controlling pulse width of the first channel output pulse train as a function of the stored digital data representative of the first amplitude control signal during an execute mode to reproduce the desired FES regimen.

40. The method of claim 39 and selecting a pulse repetition rate of the first channel output pulse train.

41. The method of claim 39 and further including:
producing a second channel output pulse train;
providing a second amplitude control signal;
controlling the pulse amplitude of the second channel output pulse train as a function of the second amplitude control signal during the program mode to produce the desired FES regimen;
storing digital data representative of the second amplitude control signal; and
controlling pulse width of the second channel output pulse train as a function of the stored digital data representative of the second amplitude control signal during an execute mode to reproduce the desired FES regimen.

42. The method of claim 41 and selecting a repetition rate of second channel output pulse train.

43. The method of claim 39 and controlling pulse width of a second channel output pulse train as a function of the stored digital data representative of the first amplitude control signal during the execute mode.

* * * * *